United States Patent [19]

Guidelli et al.

[11] Patent Number: 4,548,679

[45] Date of Patent: Oct. 22, 1985

[54] HANGING MERCURY DROP ELECTRODE CAPABLE OF AUTOMATIC CONTROL

[75] Inventors: Rolando Guidelli; Maria L. Foresti, both of Rome, Italy

[73] Assignee: Consiglio Nazionale Delle Ricerche, Rome, Italy

[21] Appl. No.: 556,065

[22] Filed: Nov. 29, 1983

Related U.S. Application Data

[63] Continuation-in-part of Ser. No. 458,342, Jan. 17, 1983, abandoned.

[30] Foreign Application Priority Data

Aug. 9, 1982 [IT] Italy ................................. 22785 A/82

[51] Int. Cl.$^4$ ............................................ G01N 27/34
[52] U.S. Cl. ..................................... 204/1 T; 204/413
[58] Field of Search ......................... 204/1 T, 400, 413

[56] References Cited

U.S. PATENT DOCUMENTS

| | | | |
|---|---|---|---|
| 2,361,295 | 10/1944 | Kanner et al. | 204/413 |
| 2,728,721 | 12/1955 | Ladisch et al. | 204/413 |
| 3,367,858 | 2/1968 | Kurosaki | 204/413 |
| 3,410,763 | 11/1968 | Capuano | 204/413 |
| 3,421,989 | 1/1969 | Haagen-Smit | 204/413 |
| 4,138,322 | 2/1979 | Barnes et al. | 204/413 |
| 4,142,944 | 3/1979 | Smith | 204/413 |

OTHER PUBLICATIONS

Schiffrin, *J. Electroanal. Chem.*, vol. 23, No. 1, (1969), pp. 168-171.

Birch et al., *Analytical Chemistry*, vol. 39, No. 10, Aug. 1967, pp. 1182-1184.

Reprint of *Analytical Chemistry*, vol. 45, No. 14, pp. 2442-2443, Dec. 1973.

*Primary Examiner*—T. Tung
*Attorney, Agent, or Firm*—Bucknam and Archer

[57] ABSTRACT

A hanging mercury drop electrode is described which makes use of a capillary tube with an inverted-U shape, removably fastened to an air-tight pressure-resistant cylindrical mercury reservoir. The capillary tube has a sufficiently thin inner diameter ($0.35 \times 10^{-2}$ to $0.5 \times 10^{-2}$ cm) and a sufficient length (40 to 50 cm) such that the viscous forces prevent mercury from flowing through the capillary tube, once a height of the mercury head is selected (1 to 2 cm) which roughly counterbalances the back-pressure acting on the drop surface. To increase the drop size, a pressure higher than the atmospheric pressure is transmitted to the mercury reservoir from a pressure generator via an electromechanical valve, which is controlled by a timer or a microprocessor. The drop becomes stationary as soon as the mercury reservoir is connected with the outer atmosphere via another electromechanical valve. A whole cycle of operations of the present electrode comprises: (1) detachment of a preformed drop by a hammer which knocks the capillary tube; (2) growth of a new drop by application of a pressure higher than the atmospheric pressure to the mercury reservoir; (3) blockage of the drop area by application of the atmospheric pressure to the mercury reservoir; (4) desired electroanalytical measurement on the resulting static mercury drop.

14 Claims, 3 Drawing Figures

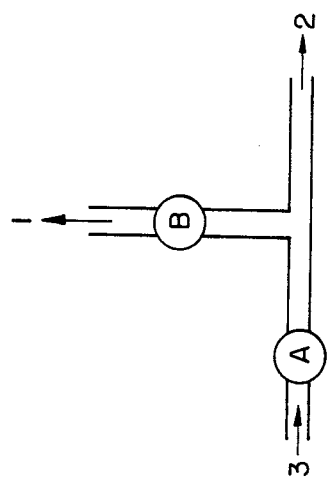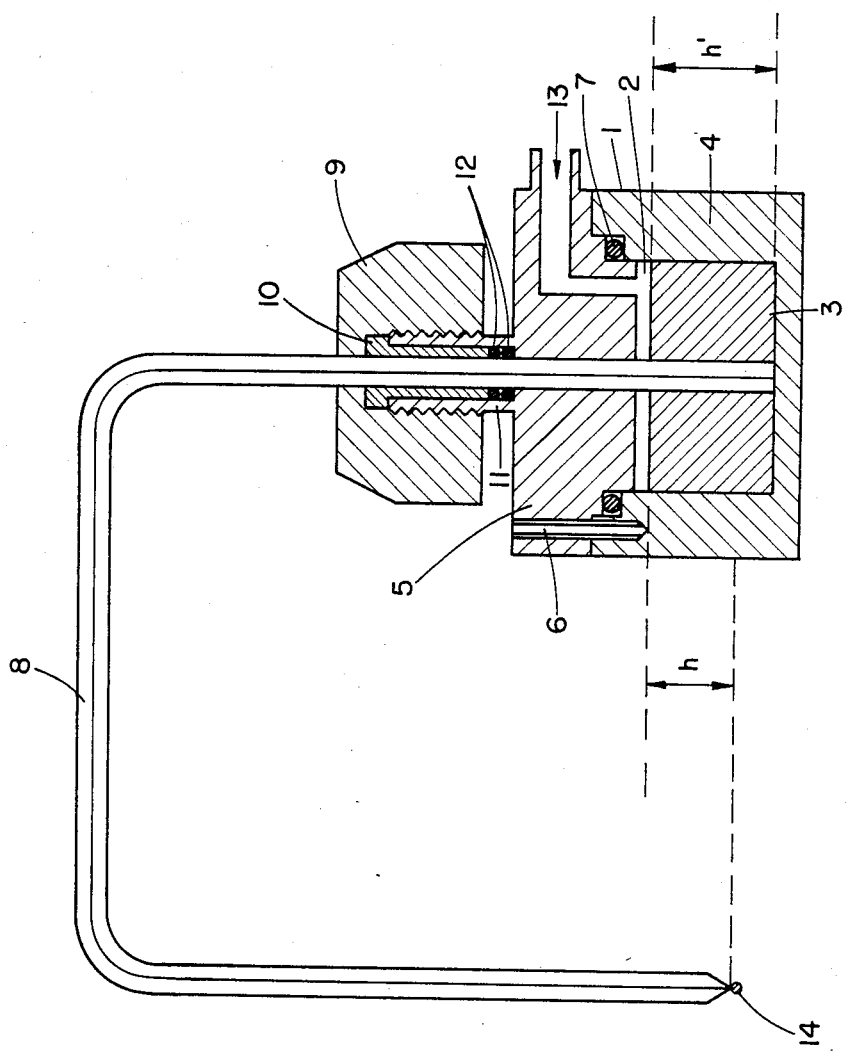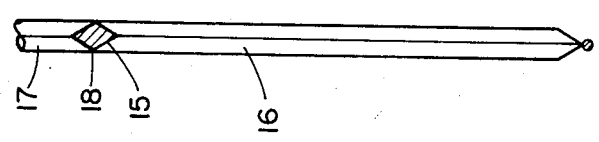

HANGING MERCURY DROP ELECTRODE CAPABLE OF AUTOMATIC CONTROL

This is a continuation-in-part of Ser. No. 458,342, filed Jan. 17, 1983, now abandoned.

The present invention relates to a hanging mercury drop electrode, and more particularly to a control for the formation of hanging drops which does not make use of valves.

Polarography, one of the most widespread electroanalytical techniques, makes use of a dropping mercury electrode, consisting of a vertical fine-bore capillary tube above which a constant head of mercury is maintained and from which mercury flows dropwise. The dropping mercury electrode is dipped into an electrolysis cell containing about 5 to 50 ml of solution. The inner diameter of the capillary is about $0.5 \times 10^{-2}$ to $0.8 \times 10^{-2}$ cm and the capillary is connected by tubing to a mercury reservoir, which is placed to 30 to 80 cm above the capillary orifice. By varying the height of the mercury head, the pressure of the mercury column can be adjusted to give a drop time of about 2 to 8 sec. Atmospheric oxygen is removed from the solution by bubbling an inert gas through the solution. A reference electrode is present in the solution along with the dropping mercury electrode, and the electrochemical circuit is formed by connecting the cell to a potentiometer, which permits the application of any electric potential between the dropping mercury electrode and the reference electrode. If the solution contains a reducible substance, then a current due to electroreduction of this substance starts to flow as the applied potential is made sufficiently negative. With increasing negative potential, this current attains a maximum limiting value, which is proportional to the bulk concentration of the reducible substance and is employed for a quantitative analysis of this substance. A major advantage of the dropping mercury electrode over other varieties of electrodes is represented by the periodical renewal of its surface area, which minimizes surface contamination, thus permitting highly reproducible measurements. A disadvantage of this electrode is represented by the capacitive current, which is produced by the growth of the mercury drop. This current does not depend on the presence of the reducible substance in the solution, and hence interferes with obtaining accurate polarographic measurements. This drawback can be overcome by using a static mercury drop hanging at the end of a capillary tube. A hanging mercury drop is also required in stripping voltammetry, a widespread electrochemical technique for trace analysis of metal ions. With this technique metal ions present in the solution at a trace level are electroreduced at a hanging mercury drop for a sufficiently long time (usually several minutes) and concentrated within the drop under the form of an amalgam. The metal is then stripped from the amalgam and electrooxidized back into the solution by shifting the applied potential towards positive values. The resulting oxidation current, when recorded against the applied potential, yields a peak whose area measures the concentration of the metal ion in the solution.

A prior art technique for preparing hanging mercury drops establishes a static drop at the end of a capillary tube by selectively decreasing the height of the mercury column after formation of a drop, to prevent further drop growth. Such a system has little commercial value because it allows neither a rapid renewal of each drop nor its rapid replacement by a further drop of identical surface area, and hence is unsuitable for repetitive measurements.

Another prior art technique makes use of a microsyringe with a micrometer for control of drop size. The hanging drop is formed at the tip of a capillary tube via displacement of mercury in the calibrated micrometer syringe delivery system. A basic disadvantage of this prior art technique is the small volume of the mercury reservoir enclosed in the microsyringe, and the resulting need of frequent fillings of the reservoir. During the filling operation small pockets of air are frequently trapped in the reservoir. Even the smallest pockets of air seriously interfere with the stability of the hanging mercury drop. In fact these pockets, on account of their compressibility, transmit vibrations to the drop. Moreover, as soon as a drop is detached from the capillary tip, any pockets of air contract causing the solution to creep into the capillary and, hence, to contaminate it. Furthermore, even the smallest amount of air may sporadically break loose and flow down the capillary causing a break in the electrical connection.

Another form of prior art mercury electrodes employs a dropping mercury capillary with an enlarged bore at its upper end. The mercury flow of the dropping mercury electrode is stopped at selected time intervals to produce a static rather than a growing drop, by obstructing this bore with a steel needle or a plunger. The use of a sliding gate valve to be periodically opened and closed has also been suggested in order to form static drops at regular time intervals. A shortcoming of all these electrodes, in which the mercury flow is stopped at selected time intervals by obstructing the mercury pathway mechanically, is that bubbles of air are inevitably trapped against the capillary bore and around the needle or plunger. Another shortcoming is that a prolonged use of these electrodes leads to mercury leakage across the seal between the bore and the plunger, owing to the wear or progressive mismatching resulting from bore-to-plunger friction.

The only prior art mercury electrode in which the mercury flow is stopped at selected time intervals without obstructing the mercury pathway has been described by Diaz et al.[1]. It consists of a capillary connected to a mercury reservoir. The mercury flow is stopped by rapidly creating a depression on the mercury reservoir. This goal is achieved by connecting the mercury reservoir, through a solenoid valve, to a ballast maintained at an adjustable pressure less than the atmospheric pressure. The depression in the ballast is adjusted to the value appropriate for stopping the mercury flow by means of a mercury barometic sensor, which is calibrated by following any changes in drop area by a.c. impedance measurements. A drawback of this prior art hanging mercury drop electrode is the need of a rather involved calibration, without which the applied depression may equally well contract the mercury drop, stop it or expand it at a lower rate. A further drawback is connected with the use of the mercury barometric sensor, which is subject to sticking of the mercury against the glass tubing.

[1] J. Electroanal. Chem., 130, 345-349, 1981

It is an object of the present invention to provide a hanging mercury drop electrode for periodically generating static mercury drops of reproducible size at the end of a capillary, wherein objectionable features inherent in prior art devices are eliminated.

It is another object of the present invention to provide a device of the character described wherein the drop area remains constant for an indefinitely long time, without the use of valves obstructing the mercury pathway mechanically or without selectively decreasing the height of the mercury head after formation of each single drop.

It is still another object of the present invention to provide a device of the character described wherein air does not interfere with the operation of filling both the mercury reservoir and the capillary at the end of which the static mercury drop is formed.

Another object of the present invention is to provide a device of the character described wherein the capillary holding the static drop is readily replaceable without trapping bubbles of air into the mercury pathway.

A still further object of the present invention is to provide a device of the character described having greater reliability than those described in the prior art and in which the apparatus is less complicated in use and less expensive to manifacture.

Additional objects and advantages of the present invention will appear from the following description and the accompanying drawings.

To achieve the foregoing objects and in accordance with the purposes of the invention, the hanging mercury drop electrode according to the present invention comprises a mercury reservoir for liquid mercury or other similar liquid and a capillary removeably fastened to the reservoir. The capillary tube has first and second ends, with a capillary passage between them; the first end is immersed in the mercury of the reservoir and the second end, which holds the hanging mercury drop, is immersed in the elctrolytic solution to be examined. The main structural features of the electrode which distinguish it from all prior art mercury electrodes are that the capillary tube is sufficiently long, and of a sufficienty small inner diameter, and that the level of the second capillary end is sufficiently close to the upper level of the mercury pool in the reservoir, so that viscous forces prevent mercury from flowing through the capillary when the mercury reservoir and the second capillary end are both subject to the same atmospheric pressure.

In a preferred embodiment of the present invention the capillary tube has an inverted-U shape, an inner diameter between $0.35 \times 10^{-2}$ and $0.5 \times 10^{-2}$ cm, and a length between 40 and 50 cm. With the foregoing structural features, the flow of the mercury through the capillary tube is completely prevented by setting the level of the second capillary end lower than the upper level of the mercury pool in the reservoir by approximately 1 to 2 cm, so as to roughly counterbalance the back-pressure. Incidentally, the back-pressure is the pressure, due to interfacial tension forces, which acts at the surface of a mercury drop and tends to contract the drop volume by squeezing the mercury from the drop back into the capillary tube. In the absence of the back-pressure and with the same atmospheric pressure acting both on the mercury reservoir and on the second capillary end, the driving force which causes the mercury to flow through the capillary is measured by the pressure of a mercury column of height equal to the difference between the level of the second capillary end and the upper level of the mercury pool in the reservoir. This pressure is frequently referred to as the height of the mercury head. Hence, the back-pressure, which tends to contract the drop volume and amounts to about 10 to 20 mm of Hg, is approximately counterbalanced by setting the level of the second capillary end lower than the upper level of the mercury pool in the reservoir by about 1 to 2 cm. With this configuration, a change in the difference between the above two levels by 1 cm in any of the two possible directions is not sufficient to cause a flow of mercury through the capillary tube, thanks to viscous forces, with the result that any preformed hanging mercury drop maintains a constant surface area for an indefinitely long time, provided that the same gas pressure acts on the mercury reservoir and on the second capillary end. The size of the hanging mercury drop can only be increased by applying to the mercury reservoir a pressure higher than the atmospheric pressure, which acts on the second capillary end. Hence, upon dislodging any preformed hanging mercury drop by imparting to the capillary a mechanical shock with a suitable hammer, a new drop can be formed by applying to the mercury reservoir a pressure sufficiently higher than the atmospheric pressure; the growth of this new drop can then be interrupted at a predetermined time, giving rise to a static mercury drop, by merely connecting the mercury reservoir with the outer atmosphere.

The objects and advantages of the present invention may be better appreciated by a detailed description taken in conjunction with the two following drawings, wherein:

FIG. 1 is a sectional diagram of a preferred embodiment of a hanging mercury drop electrode according to the teachings of the present invention;

FIG. 2 is a block diagram of the system of two electromechanical valve employed for applying, at different times, the atmospheric pressure and a higher pressure to the mercury reservoir.

Referring to FIG. 1, the hanging mercury drop electrode comprises a housing 1 forming a reservoir 2 for liquid mercury 3. The housing 1 is formed on any material which is chemically inert with respect to mercury and resistant to the pressures to be applied to the reservoir. For maximum pressures less than 6 to 7 Atm, a convenient material is plexiglass, which allows the mercury level in the reservoir to be constantly monitored. For higher maximum pressures, stainless steel is conveniently employed. In the latter case, the mercury level in the reservoir can be monitored through a plexiglass window, located on the upper portion of the sidewalls of the mercury reservoir and not represented in FIG. 1. It should be realized that other liquids can be substituted for mercury and employed according to the teachings of the present invention. Hence, in what follows the term mercury is intended to refer to mercury as well as to other substitutable liquids. The housing 1 in FIG. 1 consists of cylindrical shaped sidewalls 4 and of a cover 5, which is held fast against the upper end of the sidewalls of housing 1 by screws or other suitable fastening devices 6. O-ring 7 ensures that the seal between cover 5 and sidewalls 4 is air-tight and pressure-resistant. The U-shaped capillary 8, previously described, is held fast to cover 6 by inserting it into the threaded nut 9 and the ferrule 10, which is housed in the threaded cylindrical protuberance 11 at the center of cover 5. Nut 9 is then screwed to protuberance 11, so as to compress the O-rings 12 and to make the seal between capillary 8 and cover 5 air-tight and pressure-resistant. The mercury reservoir is connected either with the outer atmosphere or with a pressure generator via opening 13 in cover 5.

The height of the mercury head, namely the difference between the upper level of the mercury pool in the reservoir and the level of the second capillary end (denoted by h in FIG. 1) can be automatically adjusted to the desired value 1 to 2 cm by adopting the following structural features. Let the mercury reservoir be filled with mercury so that the difference between the upper and the lower level of the mercury pool equals h' (see FIG. 1). The U-shaped capillary is then cut in such a way that the difference in level between the second and the first capillary end equals (h'-h); upon causing the first capillary end, namely the one immersed in the mercury pool, to touch the bottom of the mercury reservoir, the height of the mercury head is automatically adjusted to the desired value h. To avoid obstruction of the first capillary end by the bottom of the reservoir, it is sufficient to cut this end along a plane which is not exactly perpendicular to the capillary axis. For a given U-shaped capillary tube, the appropriate height h' of the mercury pool is ascertained by monitoring the upper level of the pool through the plexiglass window of the reservoir, if the latter is made of stainless steel, or directly through the sidewalls of the reservoir, if it is made of plexiglass. Naturally, the pool height h' decreases gradually during continuous operation of the electrode, and hence h decreases accordingly. Nonetheless, by selecting a sufficiently larger inner diameter for the reservoir (4 cm for the reservoir depicted in FIG. 1), the continuous operation of the electrode for one day produces a decrease in h' by no more than 0.5 cm. As previously stated, with such a change in h' the mercury continues to be prevented from flowing through the capillary, when the gas pressure acting on the mercury reservoir is equal to that acting on the second capillary end. In other words, one day of continuous operation is not sufficient to cause a decrease in h' below the critical value at which the back-pressure starts to contract the mercury drop, albeit very slowly, when the mercury reservoir is connected with the outer atmosphere. The original level h' may be easily restored when operating is started again on the following day.

A preferred embodiment for automatic operation of the present hanging mercury drop electrode makes use of two electromechanical valves A and B, schematically depicted in FIG. 2. The two electromechanical valves may be actuated either by a simple timer or by a microprocessor. Inlet 1 is connected with the outer atmosphere, inlet 2 with the mercury reservoir, and inlet 3 with a generator of a constant pressure higher than the atmospheric one. By opening valve A and simultaneously closing valve B, the pressure generator is directly connected with the mercury reservoir. Hence the constant high pressure acting on the mercury reservoir pushes mercury through the capillary, causing the volume of the mercury drop to increase proportionally in time. To block the volume of the mercury drop, the states of the two electromechanical valves are reversed, by closing valve A and simultaneously opening valve B. In this way the mercury reservoir is directly connected with the outer atmosphere and the pressure on the mercury reservoir falls abruptly to the atmospheric value, with a resulting abrupt stoppage of the growth of the mercury drop. Under these conditions the mercury drop is held stationary, and can be used in connection with any known voltammetric measuring technique which requires a stationary drop. To form a new drop, the preceding drop is dislodged by imparting a mechanical shock to the capillary by means of an electromechanical hammer which is not shown in the figures and which is actuated by the same timer or microprocessor actuating the electromechanical valves. The above mentioned cycle of operations is then repeated. Thus, by again opening valve A and simultaneously closing valve B, a new drop is formed, which is first blocked by reversing the states of the two valves and is then dislodged by the hammer.

A simple and convenient pressure generator consists of a cylinder of nitrogen or of another inert gas. This cylinder is connected to inlet 3 of FIG. 2 via an ordinary pressure reducer supplied with a 25 Atm pressure gauge. If the cylinder is opened or closed only by means of its own handle, while keeping the handle of the pressure reducer in a fixed position, the pressure supplied by the cylinder whenever it is opened remains constant in time for several months.

The weight attained by a static mercury drop after stopping the mercury flow equals $t \times m$, where t is the time, in seconds, during which the drop was caused to grow under the action of the pressure trasferred from the nitrogen cylinder to the mercury reservoir, and m is the resulting mercury flow-rate, in grams per second. Hence, the desired final size of the static mercury drop may be attained by choosing different sets of t and m values. In particular, the time t which is required to form a static mercury drop can be reduced at will by increasing the pressure transferred from the nitrogen cylinder to the reservoir, and hence the resulting mercury flow-rate m. Using a capillary tube of inner diameter between $0.35 \times 10^{-2}$ and $0.5 \times 10^{-2}$ cm, the maximum diameter attained by mercury drop 14 of FIG. 1, when the drop is immersed in air rather than in an electrolytic solution, amounts to about 1.3 mm.

The operation of filling the reservoir with mercury is readily carried out by removing cover 5, after having unscrewed it from the sidewalls 4 of the mercury reservoir. The same operation may also be carried out more simply by removing capillary 8 from cover 5, after having unscrewed nut 9, and by pouring mercury through the opening in cover 5 left free from the capillary. During filling, the upper level of the mercury pool is monitored through the plexiglass window if the reservoir is made of steel, or directly through the sidewalls, if the reservoir is made of plexiglass.

The filling operation of the U-shaped capillary 8 is carried out in a very simple way by merely fastening the empty capillary to cover 5, with the first capillary end immersed in mercury pool 3, and by applying a pressure higher than the atmospheric pressure to the mercury reservoir by means of the pressure generator. During this filling operation air bubbles are by no means trapped into the capillary. After having filled the U-shaped capillary 8 completely, it can be removed from the mercury reservoir and its two ends can be exposed to air without any loss of mercury from the capillary ends. Thus, upon removing the filled capillary from the reservoir, upon subsequently filling the reservoir with mercury up to the desired level through protuberance 11, and upon inserting the capillary again into the reservoir, the present hanging mercury drop electrode is once again ready to work.

Another preferred embodiment of the present invention makes use of an U-shaped capillary tube which differs from that previously described by the fact that its second end, which holds the mercury drop, has an inner diameter larger than that, from $0.35 \times 10^{-2}$ to $0.5 \times 10^{-2}$ cm, of the remaining part of the capillary tube. In practice, this result is achieved by soldering to a capillary tube of inner diameter between $0.35 \times 10^{-2}$ and $0.5 \times 20^{-2}$ cm, a segment of capillary tube of a larger inner diameter (e.g., 0.02 cm). A schematic picture of the second capillary end in accordance with this further preferred embodiment is shown in FIG. 1a. The connection 15 between the larger capillary tube 16 and the thinner capillary tube 17 shows an enlargement, to which a platinum wire 18 is directly soldered. While the capillary tube 17 of inner diameter between $0.35 \times 10^{-2}$ and $0.5 \times 10^{-2}$ cm practically determines the flow rate of mercury for a given applied pressure, the capillary tube 16 of larger inner diameter determines the maximum size of the hanging mercury drop. This size is obviously greater than that attained with an U-shaped capillary tube of constant inner diameter between $0.35 \times 10^{-2}$ and $0.5 \times 10^{-2}$ cm up to the second capillary end. Such a greater size represents an advantageous feature in several electroanalytical applications of the hanging mercury drop electrode. Another advantageous feature is that the electrical connection of the hanging mercury drop electrode with any electronic apparatus for electrochemical measurements can be made via the platinum wire. Under these conditions the electrical resistance of the hanging mercury drop electrode is that of the mercury thread in glass tube 16 of FIG. 1a, and hence it is much less than the electrical resistance of the hanging mercury drop electrode in accordance with FIG. 1, which is given by the resistance of the longer and much thinner mercury thread in the whole glass tube 8. A disadvantage in the use of the composite capillary tube in FIG. 1a is that the filling operation of this capillary requires a greater care. In fact, to exclude the presence of small pockets of air within enlargement 15 of FIG. 1a, the filling operation should be preferably carried out by using a vacuum pump, as is usually done with the commercially available manual hanging mercury drop electrodes. With the preferred embodiment of FIG. 1a, however, the filling operation of the capillary tube is carried out una tantum, and independent of the filling operation of the mercury reservoir. In fact, once the U-shaped capillary tube is filled, it remains filled even if it is removed from the mercury reservoir thus exposing its two ends to the air.

The reproducibility of the drop area of the electrode in accordance with the present invention was verified by measuring the change in capacitive charge following a jump in the electric potential applied to the electrode at a predetermined time, measured from the blocking of each single drop, over a series of 100 successive drops. This reproducibility was found to be better than 0.05%. The attainment of such a high degree of reproducibility was made possible by eliminating any manual intervention.

The constancy of the area of each single drop in time, during the "blockage" period in which the mercury reservoir is connected with the outer atmosphere, was verified by measuring, at regular time intervals, a faradaic current flowing across the drop. It was thus ascertained that in 10 minutes, the drop area undergoes changes which are surely less than 1%, which is the limit of sensitivity of the method employed by us for measuring the changes in the area of each single drop.

The advantages of employing the hanging mercury drop electrode according to the present invention are many. For example, it provides a substantial advancement over the prior art techniques of establishing stationary mercury drops for long periods, with regard both to the simplicity of construction and the ease of use. Thus, as outlined above, the present hanging mercury drop electrode does not make use of valves to obstruct the mercury pathway, and hence is entirely secure against air leaks into the mercury column and free from any pockets of air which might be trapped around valves. The fact that the electrode according to the present invention does not contain valves, needles, plungers or other sealing devices along the mercury pathway, not only makes it less expensive to manifacture, but it also makes it more durable; in fact, the prolonged use of sealing devices produces mercury leakage, owing to wear or progressive mismatching resulting from friction between the sealing device and the housing in which it is mounted.

While particular embodiments of the present invention have been previously shown and described, it will naturally be possible for one skilled in the art to effect certain modifications and improvements without departing from the spirit of the invention; hence, it is intended that the scope of the invention is not determined strictly by the foregoing examples but also and mainly by the scope of the appended claims.

What is claimed is:

1. A dropping mercury electrode which operates with a drop of mercury which comprises a holding mercury reservoir, a first capillary tube of inverted U-shape, one end of the tube being free, said mercury drop being formed on said free end, the other end being dipped in said mercury reservoir, said capillary tube being of a sufficiently small length and of a sufficiently small inner diameter and the level of said free end being held at a constant and sufficiently small difference below the upper level of the mercury in said reservoir that viscous forces prevent mercury from flowing through said capillary tube when said capillary end holding said capillary drop and said reservoir are both subject to the same atmospheric pressure and wherein said first capillary tube of inverted U-shape has an internal diameter between $0.35 \times 10^2$ and $0.5 \times 10^{-2}$ cm and has a length of 40 to 50 cm.

2. The electrode according to claim 1 which is provided with a system of electrovalves, said electrovalves being used to apply and discontinue pressure exerted by an inert gas on the mercury in said reservoir.

3. The electrode according to claim 2 wherein said inert gas is nitrogen, compressed air or another inert gas which is applied from a cylinder and the cylinder is provided with means for reducing the pressure and for adjusting the pressure between 3 and 12 atmospheres and the drop of mercury is blocked by restoring the atmospheric pressure by establishing communication between said mercury reservoir and the external environment.

4. The electrode according to claim 1 wherein the free end of said first capillary tube is at a level lower with respect to the mercury reservoir of about 1–1.5 cm.

5. The electrode according to claim 1 wherein a second capillary tube of greater internal diameter is soldered to said first capillary tube of internal diameter between $0.35 \times 10^2$ and $0.5 \times 10^{-2}$ cm.

6. The electrode according to claim 5 wherein said first capillary is connected to said second capillary and a platinum wire is directly soldered to the connection point between said first and second capillary.

7. A method of rapidly generating static mercury drops of reproducible size and of holding them for an indefinitely long time at one end of a capillary tube immersed in a solution subject to the atmospheric pressure, the other end of said capillary tube being connected to a mercury reservoir, which method comprises:

(a) setting the level of said capillary end holding said mercury drop lower than the upper level of the mercury pool in said reservoir by about 1 to 2 cm, so as to roughly counterbalance the back-pressure;

(b) choosing said capillary tube of a sufficient length and of a sufficiently small inner diameter such that, in conjunction with said difference in level, viscous forces prevent mercury from flowing through said capillary tube when said mercury reservoir is subject to the atmospheric pressure;

(c) causing the mercury to flow through said capillary tube and hence said mercury drop to grow by application of a pressure higher than the atmospheric pressure to said mercury reservoir;

(d) limiting the surface area of said mercury drop after attainment of the desired size by rapidly switching the pressure on said mercury reservoir to the atmospheric value.

8. A method of periodically generating static mercury drops of reproducible size which comprises using the method defined in claim 7 and further comprising the following steps:

(a) dislodging of a static drop by imparting to said capillary tube a mechanical shock;

(b) forming of a new drop by connecting said mercury reservoir for a predetermined period of time to a pressure generator so as to subject said reservoir to said pressure higher than the atmospheric pressure and to cause the growth of said new drop;

(c) limiting the surface area of said new drop by connecting said mercury reservoir with the outer atmosphere;

(d) using said new static drop for any desidered electrochemical or electroanalytical measurements; and (e) repetition of the steps (a)-(d).

9. The method recited in claim 8 wherein the various steps are performed under the control of an electronic timer.

10. The method recited in claim 8 wherein the various steps are performed under the control of a microprocessor.

11. The method recited in claim 8, wherein said mercury reservoir, made of some pressure-resistant material inert to mercury, is connected with a pressure generator consisting of a cylinder of an inert gas via a pressure reducer and an electromechanical valve during said step (b), and is connected with the outer atmosphere via another electromechanical valve during step (c).

12. The method recited in claim 7, wherein said capillary has an inverted U-shape, a length between 40 and 50 cm, an inner diameter between $0.35 \times 10^{-2}$ and $0.5 \times 10^{-2}$ cm and is held fast to said mercury reservoir by a suitable fastening device.

13. The method recited in claim 12, wherein the inner diameter at the end of said U-shaped capillary which holds said hanging mercury drop, and hence the maximum diameter of said mercury drop, are made larger by soldering to said capillary tube of inner diameter between $0.35 \times 10^{-2}$ and $0.5 \times 10^{-2}$ cm, a segment of a second capillary tube of larger inner diameter.

14. The method recited in claim 13, wherein electrical connection with said mercury drop is made by means of a platinum wire which is directly soldered to the connection between the two said capillary tubes of different inner diameter.

* * * * *